(12) United States Patent
Watanabe et al.

(10) Patent No.: US 6,805,961 B1
(45) Date of Patent: Oct. 19, 2004

(54) MEDICAL ADHESIVE TAPE OR SHEET, AND FIRST-AID ADHESIVE TAPE

(75) Inventors: Tetsuo Watanabe, Osaka (JP); Takashi Kinoshita, Osaka (JP); Fumiya Shirai, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/488,762

(22) Filed: Jan. 21, 2000

(30) Foreign Application Priority Data

Jan. 27, 1999 (JP) ............................................ 11-018751

(51) Int. Cl.⁷ ................................................ B32B 13/04
(52) U.S. Cl. ...................... 428/446; 428/448; 428/520; 428/523
(58) Field of Search ................................ 428/446, 448, 428/520, 523

(56) References Cited

U.S. PATENT DOCUMENTS

| | | | | |
|---|---|---|---|---|
| 3,645,835 A | * | 2/1972 | Hodgson | 161/146 |
| 4,347,844 A | | 9/1982 | Ohki et al. | 128/287 |
| 4,595,001 A | * | 6/1986 | Potter et al. | 128/156 |
| 6,002,064 A | * | 12/1999 | Kobylivker et al. | 604/367 |
| 6,063,981 A | * | 5/2000 | Wehner et al. | 604/367 |
| 6,096,014 A | | 8/2000 | Haffner et al. | 604/367 |
| 6,107,219 A | * | 8/2000 | Joseph et al. | 422/361 |

FOREIGN PATENT DOCUMENTS

| | | | |
|---|---|---|---|
| EP | 0 979 838 | 2/2000 | ............. C08J/5/18 |
| EP | 1 020 196 | 7/2000 | ........... A61L/15/24 |
| JP | 02-001284 | 1/1990 | ........... A61L/15/58 |
| JP | Hei 4-224809 | 8/1992 | |
| JP | Hei 7-276584 | 10/1995 | |
| WO | WO 99/33498 | 7/1999 | ........... A61L/15/00 |

OTHER PUBLICATIONS

European Search Report for EP 00 10 1300.

* cited by examiner

*Primary Examiner*—Peter D. Mulcahy
(74) *Attorney, Agent, or Firm*—Kilyk & Bowersox, P.L.L.C.

(57) ABSTRACT

To 100 parts by weight of a thermoplastic resin such as polypropylene resin, a blend of polypropylene resin and elastomer, or a copolymer of polypropylene resin and elastomer, 10 to 200 parts by weight of a silicic acid compound such as zeolite or talc were added to form a film for a supporting substrate. Using this film as a supporting substrate, an adhesive layer comprising an acrylic adhesive is provided on the supporting substrate to obtain a medical adhesive tape or sheet according to the present invention. An absorbent pad is provided at a central region on the surface of the adhesive layer to obtain a first-aid adhesive tape.

9 Claims, No Drawings

MEDICAL ADHESIVE TAPE OR SHEET, AND FIRST-AID ADHESIVE TAPE

BACKGROUND OF THE INVENTION

1. Field of the Invention

The present invention relates to a medical adhesive tape or sheet and a first-aid adhesive tape. More specifically, the present invention relates to a medical adhesive tape or sheet and a first-aid adhesive tape used in medical uses in fields of adhering products, particularly rolled bandage, surgical tape, plaster, poultice, dressing member, wound protector and percutaneous absorption preparation. The above-stated medical adhesive tape or sheet and a first-aid adhesive tape are also suitable for use in aged persons, infants and sickly persons, who are susceptive to irritation to their skin.

2. Description of the Related Art

Conventionally, many films comprising a plasticized polyvinyl chloride as a main component prepared by a calender method or a sol cast method have been used as various medical adhesive tapes or sheets such as a first-aid adhesive tape or a surgical tape.

A film for a supporting substrate comprising this plasticized polyvinyl chloride as a main component has the characteristic that it shows high stress at a tensile initial stage, but stress relaxation rapidly occurs with the passage of time. This stress relaxation is due to plasticity of the polyvinyl chloride film. In the case where an adhesive tape or sheet that includes a film for a supporting substrate having such a characteristic is adhered to a skin, tensile stress is gradually relaxed after the adhering, resulting in a reduction of load to the skin. Thus, with use of the supporting substrate film comprising the plasticized polyvinyl chloride as a main component, adhering workability is secured by an appropriate stress when adhering, and also a tense feeling is eliminated by the subsequent stress relaxation, so that physical irritation to the skin is alleviated. This imparts the tape or sheet with both good operability and low skin-irritating property.

However, if the plasticized polyvinyl chloride is used, a large amount of plasticizer is contained and such a plasticizer migrates from the film to the adhesive layer. As a result, there are disadvantages of a lowered adhesive force or a lowered cohesive force, the adhesive modifies, or the adhesive fluidizes to thereby stain a circumference portion of the adhering site.

Further, since the film contains chlorine atoms, there is a need for a countermeasure on its post-treatment from the standpoint of a recent environmental problem.

For this reason, there has been active development of flexible and stretchable thermoplastic resins as a substitute material of vinyl chloride, not limited on medical uses, and many thermoplastic resins have been commercialized in olefin resins, ethylene-vinyl acetate copolymer (EVA) resins or elastomer resins.

Specific examples of the commercialized products include ethylene-methacrylate (EMA) resins, amorphous poly-α-olefin resins, ethylene-vinyl acetate copolymer (EVA) resins, olefin resin/EMA blends, polyurethane resins, low density polyethylene (LDPE), linear low density polyethylene (LLDPE) resins and ethylene-methyl methacrylate copolymer (EMMA) resins. Of those, from the standpoint of providing elastic, non-chlorine-containing material, thermoplastic elastomer (TPE) resins have been recently actively investigated as an effective material that achieves the above objects.

As the thermoplastic elastomer resins, for example, styrene-based thermoplastic elastomers (SBC) such as styrene-butadiene-styrene block copolymer (SBS) were first developed, and subsequently engineering plastic-based TPE such as thermoplastic vinyl chloride-based elastomers (TPVC), thermoplastic olefin-based elastomers (TPO) or ester olefin-based elastomers (TREE) have been developed. In particular, the thermoplastic olefin-based elastomers (TPO) are in a position most close to polyvinyl chloride in weather resistance and cost.

Further, in recent years, an improved TPO to be scratchless has been developed, and this improved TPO includes a polypropylene-based polymer alloy obtained by blending a novel, high blend-type hydrogenated styrene-butadiene copolymer (hydrogenated SBR).

Those various resins may be used as a substitute of the vinyl chloride resins; however, a portion of the above thermoplastic elastomers is merely utilized for medical uses only in areas such as an infusion bag, a waste bag for artificial dialysis or infusion tube.

On the other hand, it is attempted to apply flexible olefins such as the above-described amorphous poly-α-olefin resins as a substitute film of the vinyl chloride resins to a medical film for a supporting substrate. However, it cannot be said that those are the most appropriate, in view of the following points.

That is, there has been the problem of very poor operability for adhesion in actual spots of medical treatment even if the flexible olefins are low in stress no matter how strong tension or elongation exerted thereon is. Alternatively, when the rubber elasticity is too high, the stress upon deformation becomes too high to the contrary, resulting in that a tension is successively exerted on the skin while the tape or sheet is being adhered so that there occurs an increased physical irritation to the skin.

Thus, opposite properties of good operability for adhesion and low irritating property to the skin cannot sufficiently be satisfied if the conventional vinyl chloride-free resins are only directly used as a film for a supporting substrate of a medical adhesive tape or sheet.

From this standpoint, there have been several proposals for utilization of thermoplastic elastomers as a film for supporting substrate of a medical adhesive tape having the same stress relaxation property as in the vinyl chloride resins. Thermoplastic resins having such a high stress relaxation property include olefin-based resins blended with large amounts of rubber components and amorphous olefin-based resins.

In the conventional olefin-based thermoplastic elastomers, a blend-type thermoplastic elastomer in which a polypropylene (PP) is a hard segment and an ethylene-propylene rubber (EPR) is a soft segment has been a leading elastomer. However, in the case of PP/EPR, which is a general simple blend, it has been difficult to blend therewith a large amount of rubber in a uniformly dispersed state so that it has been difficult to sufficiently exhibit merits of alloy formation (i.e., achieving both heat resistance and flexibility, improvement in stress relaxation.

On the other hand, to solve the problems, the system in which polymer alloy is produced in the step of polymerization has been developed.

Examples of the olefin-based thermoplastic elastomers (reactor TPO) that can directly be produced at the polymerization step include FPO (Flexible Poly Olefins) of Rexene Co., Catalloy resin of Montell Polyolefins Co. and PER resin of Tokuyama Soda Co.

Catalloy resin is a resin obtained by alloying an ethylene-propylene rubber in an olefin resin at the polymerization step, and has excellent characteristics in heat resistance, tear strength and piercing strength as compared with other flexible resins (such as PVC or PE-based resins). The resin is obtained by a polymerization process technique that enables a polyolefin to be alloyed in a polymerization reactor. The polymerization process technique comprises multi-stage gas phase polymerization reactors, in each of which polymerization is independently conducted, and a polymer obtained in the respective reactor is taken out in an alloyed state as a final product. In this process, a synthetic rubber (ethylene-propylene rubber) is blended at the polymerization step, and a polymer resin having considerably high rubber content is obtained as compared with blending with an extruder or the like. As a result, it is possible to closely harmonize high elasticity of polyolefin and flexibility of rubber, so that the alloyed resin can have high initial elastic force and rapid stress relaxation property.

Further, examples of the amorphous olefin-based resin include APAO (Amorphous Poly Alpha Olefin) resin and CAP resin, products of Ube Industry Co. Those resins are excellent in flexibility and heat resistance and are also relatively excellent in stress relaxation property, as compared with the conventional olefin-based resins.

APAO resins are seldom used alone but they are blended with polypropylene or commercialized as a multilayer film having laminated thereon an outer layer of other olefin-based resin. In such a case, they have relatively high stress relaxation property.

SUMMARY OF THE INVENTION

However, even if the above Catalloy resin or amorphous poly-α-olefin-based resin is used, an initial stress is virtually too high, so that there may the case where a tense feeling just after adhering is strong. Further, relaxation tendency becomes extremely dull after relaxation has occurred to a certain degree or more, so that there is the tendency that a limit is observed in achieving flexibility by stress relaxation. Furthermore, the speed of stress relaxation leading to flexibility is clearly lower than that of the film composed of flexible polyvinyl chloride resin. In particular, even a small load to a skin, if it remains sustained, may cause some users an apparent irritation to the skin.

Further, the above resins not only give a poor feeling but also poor appearance when they are used in a medical adhesive tape or a first-aid adhesive tape.

The present invention has been made in view of the above-described disadvantages.

Accordingly, it is an object of the present invention to provide a medical adhesive tape or sheet, and a first-aid adhesive tape, suitable for adhering to bending portions or the like by using a supporting substrate having appropriate flexibility and stress relaxation property as well as good feeling as a substitute of a film for a supporting substrate made of a polyvinyl chloride resin.

As a result of intensive investigations, the present inventors have found that the above object can be achieved by using a composition containing a thermoplastic resin and a silicic acid compound in certain proportions for a supporting substrate. The present invention has been completed based on this finding.

More specifically, the present invention provides the followings:

1) A medical adhesive tape or sheet comprising a supporting substrate and an adhesive layer directly or indirectly laminating thereon, wherein the supporting substrate comprises a composition which comprises 100 parts by weight of a thermoplastic resin and 10 to 200 parts by weight of a silicic acid compound.

2) The medical adhesive tape or sheet as described in 1) above, wherein the silicic acid compound is at least one selected from the group consisting of zeolite, talc and silica.

3) The medical adhesive tape or sheet as described in 1) above, wherein the thermoplastic resin is at least one member selected from the group consisting of a polypropylene resin, a blend of a polypropylene resin and an elastomer, and a copolymer of a polypropylene resin and an elastomer.

4) The medical adhesive tape or sheet as described in 3) above, wherein the polypropylene resin, or the copolymer of a polypropylene resin and an elastomer is amorphous or low crystalline.

5) The medical adhesive tape or sheet as described in 4) above, wherein the amorphous or low crystalline polyolefin resin is present in an amount of 30 to 100% by weight based on the total weight of film-forming materials for a supporting substrate.

6) The medical adhesive tape or sheet as described in 1) above, wherein the supporting substrate further comprises a resin modifier.

7) The medical adhesive tape or sheet as described in 6) above, wherein the resin modifier is present in an amount of 0.1 to 40% by weight based on the total weight of the film-forming resin composition.

8) The medical adhesive tape or sheet as described in 6) above, wherein the resin modifier is at least one selected from the group consisting of a hydrogenated product of styrene-butadiene copolymer or its maleic acid-modified product, polystyrene-polyethylene.butylene-crystalline polyolefin, crystalline polyolefin-polyethylene.butylene-crystalline polyolefin, ethylene-ethyl acrylate copolymer, ethylene-acrylic acid ester-maleic anhydride copolymer, ethylene-methacrylic acid glycidyl ester copolymer, maleic anhydride graft polypropylene, maleic anhydride graft ethylene-polypropylene copolymer, acrylic acid graft polypropylene, ethylene-vinyl acetate copolymer, ethylene-vinyl acetate/ethylene-propylene-diene/polyolefin graft copolymer, metal salts of ethylene-methacrylic acid copolymer and chlorinated paraffin.

9) The medical adhesive tape or sheet as described in 1) above, wherein the supporting substrate has a stress relaxation ratio of 60% or less.

10) A first-aid adhesive tape comprising the medical adhesive tape or sheet as described in 1) above, and an absorbent pad provided at a central region on a surface of the adhesive layer thereof.

The above and other objects, effects, features and advantages of the present invention will become more apparent from the following description of preferred embodiments.

DETAILED DESCRIPTION OF THE INVENTION

The adhesive tape or sheet of the present invention is intended to include either of wide sheet-like materials and narrow tape-like materials.

The thermoplastic resins used in the supporting substrate of the present invention are not particularly limited, and resins having flexibility and stretchability are preferably used. Examples of the thermoplastic resin used include polymethyl methacrylate, modified acrylic resin, low-density polyethylene, polypropylene, polystyrene, propyl cellulose, cellulose acetate, flexible polyvinyl chloride, polyvinylidene chloride, vinylidene fluoride, polyurethane and polycarbonate. Of these, halogen-free resins that do not contain chloride atoms or fluorine atoms are preferably used, considering environmental problem and the like. Those resins can be used alone or as appropriate mixtures of two or more thereof.

Of the above thermoplastic resins, it is more preferable to use blends of polypropylene resin or polypropylene resin and thermoplastic elastomer (TPE), and copolymers of polypropylene resin and thermoplastic elastomer.

When two or more of the above thermoplastic elastomers are used in combination, it is desirable to further combine the above thermoplastic resin with a resin having the properties of elastomer.

The term "elastomers" as used herein refers to crosslinked rubbers, thermoplastic elastomers (TPE), and liquid rubbers.

Liquid rubbers are highly flowable synthetic rubbers having molecular weights in the order of several thousands in contrast to ordinary rubbers having molecular weights of several ten thousands to several hundred thousands.

Elastomers are not particularly limited to specific ones. Elastomers as crosslinked rubbers include those obtained by appropriately crosslinking raw material rubbers, such as isoprene rubber (IR), butadiene rubber (BR), 1,2-polybutadiene (1,2-BR), styrene-butadiene rubber (SBR), chloroprene rubber (CR), nitrile rubber (NBR), butyl rubber (IIR), ethylene-propylene rubber (EPM, EPDM), chlorosulfonated polyethylene (CSM), acrylic rubber (ACM, ANM), epichlorohydrin rubber (CO, ECO), polysulfide rubber (T), silicone rubber (Q), methylvinyl silicone rubber (VMQ), silicone fluoride rubber (FVMQ), fluororubber (FKM), and urethane rubber (U).

Elastomers as thermoplastic elastomers include styrene-based thermoplastic elastomers (SBC) such as styrene-butadiene-styrene block copolymer (SBS), styrene-isoprene-styrene block copolymer (SIS), styrene-ethylene.butylene-styrene block copolymer (SEBS), styrene-ethylene.propylene-styrene block copolymer (SEPS), and hydrogenated styrene-butadiene random copolymer (HSBR); thermoplastic polyolefin-based elastomers (TPO) such as crystalline polyolefin-polyethylene.butylene-crystalline polyolefin (CEBC), ethylene-propylene rubber, ethylene-1-butylene rubber, ethylene-vinyl acetate copolymer, and amorphous poly-α-olefin, and blends of these, partial crosslinked products; dynamically vulcanized type polyolefin-based thermoplastic elastomers (TPV); thermoplastic polyurethane-based elastomers (TPU); polyamide-based thermoplastic elastomers (TPEA); 1,2-polybutadiene-based thermoplastic elastomers; polyvinyl chloride-based thermoplastic elastomers (TPVC); natural rubber-based thermoplastic elastomers (TPNR), fluororubber-based, thermoplastic elastomers; trans-polyisoprene-based thermoplastic elastomers; chlorinated polyethylene-based thermoplastic elastomers (CM); silicone-based thermoplastic elastomers; polyester-based thermoplastic elastomers (TPEE); ionomers; etc. Elastomers as liquid rubbers include liquid polyisoprene, liquid polybutadiene, liquid 1,2-polybutadiene, liquid styrene-butadiene rubber, liquid acrylonitrile-butadiene rubber, liquid polychloroprene, liquid poly(oxypropylene), liquid poly (oxytetramethylene) glycol, liquid polyolefin glycol, liquid poly-ε-caprolactone, liquid silicone rubber, liquid polysulfide rubber, liquid fluororubber, liquid polyisobutylene, etc.

In the case where the polypropylene resin is used alone, or a blend of the polypropylene resin and the thermoplastic elastomer or a copolymer of the polypropylene resin and the thermoplastic elastomer is used, an amorphous or low-crystalline polyolefin resin (propylene-based polyolefin) is particularly preferably used. Thus, by making a polyolefin resin in which the proportion of the crystalline portion in the resin is greatly decreased as compared with the conventional polypropylene resin, stress relaxation property and flexibility can further be improved. Further, use of such an amorphous or low-crystalline polyolefin resin is advantageous in that a large amount of the silicic acid compound can be blended.

Those amorphous or low-crystalline polyolefin resins can be used singly or by appropriately mixing two or more of them. That is, the amorphous or low-crystalline polypropylene resins can be used alone or used by blending the thermoplastic elastomer with the amorphous or low-crystalline polypropylene resin, or a copolymer of the amorphous or low-crystalline polypropylene resin and the thermoplastic elastomer can be used alone or as blends with other resins.

The proportion of the amorphous or low-crystalline polyolefin resin is preferably 30 to 100% by weight, more preferably 50 to 80% by weight, based on the total weight of the forming materials of the film for a supporting substrate. If the proportion is less than 30% by weight, it is difficult to obtain the expected stress relaxation property and flexibility.

Some methods are proposed as the representative method for producing such an amorphous or low-crystalline polyolefin resin. For example, there is the method as described in JP-A-4-224809. In this method, spherical particles having an average particle size of 15 μm obtained by co-pulverizing titanium trioxide and magnesium chloride and treating the resulting particles with n-butyl orthotitanate, 2-ethyl-1-hexanol, ethyl p-toluylate, silicon tetrachloride, diisobutyl phthalate or the like are used as a titanium-supported catalyst, and an alkyl aluminum such as triethyl aluminum is used as an aluminum compound. Further, in a polymerization tank, a silicon compound, particularly diphenyl dimethoxysilane, is added as an electron donor, and ethyl iodide is also added.

In the present invention, a crystalline polypropylene resin may be blended or copolymerized with those amorphous or low-crystalline polyolefin resins to appropriately adjust elastic modulus, elongation or the like.

The present invention can use modified amorphous or low-crystalline polyolefin resins and/or crystalline polypropylene resins. The modified resins used are obtained by modifying the amorphous or low-crystalline polyolefin or crystalline polypropylene with unsaturated carboxylic acid, such as acrylic acid, methacrylic acid, ethacrylic acid, maleic acid, fumaric acid or itaconic acid, and/or their esters, acid anhydrides, metal salts, or those derivatives.

Where the amorphous or low-crystalline polyolefin resin and the crystalline polypropylene resin are blended, the amount of the amorphous or low-crystalline polyolefin resin may be adjusted to 30 to 100% by weight, preferably 50 to 100% by weight. If the amount of the amorphous or low-crystalline polyolefin resin is less than 30% by weight, the film for a supporting substrate obtained shows strong necking to decrease stress relaxation property, and such a film is not suitable for use in the present invention.

To make the crystalline polypropylene exhibit the characteristics of a flexible film, it is preferable to use a propylene random copolymer having a melting point of 150° C. or lower.

The supporting substrate used in the medical adhesive tape or sheet of the present invention comprises a composition comprising 100 parts by weight of the thermoplastic resin above and 10 to 200 parts by weight, preferably 20 to 130 parts by weight, of the silicic acid compound.

The silicic acid compound used herein means inorganic compounds containing silicic acid, and examples thereof include zeolite, aluminum silicate, calcium silicate, bentonite, diatomaceous earth, silica, kaolin, pearlite, activated clay, mica, talc, asbestos, glass fibers, glass balloon and glass beads. Of these, zeolite, talc and silica are preferred.

In particular, zeolite has the merits in that it can improve stress relaxation property without increasing stiffness of a flexible propylene film as compared with other silicic acid compounds, and also blending of the silicic acid compound can be easily adjusted.

Zeolite is generally a general name of aluminosilicate having a three-dimensional skeleton structure, and is represented by the general formula of $xM_{2/n}O.Al_2O_3.ySiO_2.zH_2O$. In the above general formula, $M$ represents an ion-exchangeable ion, and is generally a monovalent or multivalent metal ion, n is an atomic valence of the ion-exchangeable ion (metal ion), x and y each represent a mole number of a metal oxide and silica, respectively, and z represents a mole number of water of crystallization.

Natural zeolites and synthetic zeolites can be used in the present invention. Examples of the natural zeolite include mordenite, erionite, clinobutyrolite, chabazite (rhombic zeolite). Examples of the synthetic zeolite include A type zeolite, X type zeolite, Y type zeolite, L type zeolite, and omega type zeolite. Those can be used alone or as mixtures of two or more of them.

Of those, the synthetic zeolite is more effective in that it has high purity and is excellent in uniformity of particles. On the other hand, the natural zeolite contains large amounts of impurities, but is inexpensive, which is excellent in economy. The zeolites can be appropriately selected depending on the purpose of use. They can be used in admixture.

Particle size of the silicic acid compound is not particularly limited. Silicic acid compound particles having an average particle size of 0.5 to 150 $\mu$m, preferably 0.5 to 35 $\mu$m, are suitably used. Where the silicic acid compound having a particle size larger than 150 $\mu$m is used, the occurrence of a so-called fish eye phenomenon increases in the film for a supporting substrate obtained, and this reduces the commercial value. In this regard, where the silicic acid compound having a particle size within the above-specified range is used, a film for a supporting substrate that does not have remarkable spots on the surface can be obtained. In particular, where zeolite particles are used, it is preferable to use particles having a particle size of 30 $\mu$m or less for the same reason as above. Those silicic acid compounds that are hygroscopic, such as zeolite and talc, are dehumidified before they can be molded in order to prevent the occurrence of foaming upon molding.

The supporting substrate is obtained by mixing the thermoplastic resin with the silicic acid compound. If desired or necessary, various additives or fillers can be added to the mixture. Examples of the additives include heat stabilizers, antioxidants, light stabilizers, antistatic agents, lubricants, nucleating agents, flame retardants, pigments and dyes. Examples of the fillers include various inorganic fillers such as calcium carbonate, calcium sulfate, titanium oxide, barium sulfate, magnesium hydroxide and clay and organic fillers such as synthetic fibers, e.g., polyacrylonitrile, nylon, polyester, etc.; wooden powder, pulp, cork powder; synthetic resins, e.g., polystyrene latex, urea formaldehyde particle, polyethylene powder etc.

In particular, in order to increase the stability to hindrance due to heat, oxygen in air, or light, it is preferable to add carbon black, 2,2-thio-bis(4-methyl-6-t-butylphenol), dilauryl thiodipropionate or other various known amine stabilizers and phenol stabilizers.

Further, various polymeric compatibilizers or resin modifiers are used in the mixture. As a result, deterioration of impact resistance, stretchability, flexibility, transparency or the like of the film for a supporting substrate due to the silicic acid compound can be prevented.

Examples of the polymeric compatibilizers (or resin modifiers) include hydrogenated product of styrene-butadiene copolymer or its maleic acid-modified product, ethylene-butylene macromer, ethylene-ethyl acrylate copolymer, ethylene-ethyl acrylate-maleic anhydride copolymer, ethylene-methacrylic acid glycidyl ester copolymer, maleic anhydride graft polypropylene, maleic anhydride graft ethylene-polypropylene copolymer, acrylic acid graft polypropylene, ethylene-vinyl acetate copolymer, ethylene-vinyl acetate/ethylene-propylene-diene/polyolefin graft copolymer, metal salts of ethylene-methacrylic acid copolymer and chlorinated paraffin.

Those compatibilizers (or resin modifiers) can be added generally in an amount of 0.1 to 40% by weight, preferably 2 to 30% by weight, based on the total weight of the resin composition for forming a film. If the amount is less than 0.1% by weight, either of moldability, stretchability, transparency and flexibility of the film for a supporting substrate is markedly impaired. On the other hand if the amount exceeds 40% by weight, a reduction in heat resistance of the film obtained or a reduction in workability and blocking resistance of the supporting substrate are recognized apparently. incidentally, even when the above polar group-containing ethylene copolymer was added in an amount within the above-specified range, the inherent heat resistance of the polypropylene was not impaired. Even though the film obtained was heated at 120 to 130° C. for 30 minutes or more, no denaturation, such as shrinkage, deformation or discoloration, of the film obtained was observed.

The film for a supporting substrate is molded from a mixture of the above-described components. The preparation method of the film is not particularly limited. The components are melt-kneaded under heating using various conventional kneading machines, such as various kneaders (e.g., kneader, Banbury mixer or roll), or a single-screw or twin-screw extruder, and generally once formed into pellets or mass.

The resin pellets or mass are processed into a film. The method of molding the film is not particularly limited. Conventional T-die method, inflation method, calender method or rolling method can be used for molding a film having a predetermined thickness. The film may further be subjected to a stretching processing such as vertical uniaxial stretching processing and/or horizontal uniaxial stretching processing. In particular, since the silicic acid compound is compounded, a porous film can easily be obtained by applying the stretching treatment. As a result, a supporting substrate having high moisture permeability can be obtained, and non-breathing of a skin can be after the adhering of the film. If desired, the film may further be subjected to an annealing treatment. Further, a continuous production can of course be employed such that the resin composition is kneaded and then directly formed into a film without passing through the form of resin pellets.

Thickness of the film for a supporting substrate is not particularly limited, and is appropriately determined according to the purpose of use. In general, the film is molded to have a thickness of about 2 to 1,000 μm. If the thickness is less than 2 μm, rigidity becomes insufficient and this makes it difficult to handle the film. If the thickness exceeds 1,000 μm, the film has insufficient flexibility.

Grade and blending ratio of resin, film thickness and the like are adjusted such that when the sample film having a width of 20 mm is stretched 10% in the longitudinal direction at a rate of 300 mm/min using a tensile tester having a chuck distance of 20 mm, its tensile stress just after the stretching is in a range of 200 to 2,500 gf/mm$^2$, preferably 300 to 1,600 gf/mm$^2$. If the tensile stress is lower than 200 gf/mm$^2$, the support overstretches, for example, when a rolled bandage is adhered, and advantageous features of the present invention, such as operating property in adhering, feeling or fixing property of infusion tube or the like to a skin are impaired. On the otherhand, if the tensile stress exceeds 2,500 gf/mm$^2$, flexibility is lost, and adhesiveness in adhering to a skin, follow-up property to a skin and feeling are decreased. The "londitudinal direction" used herein means a direction to which tension is liable to be received, for example, a winding direction in the case of rolled bandage or a long axis direction generally in the case of a plaster. However, where there is the great possibility that the tension is received in all directions as in a medical dressing material, the direction is not limited to one direction.

The supporting substrate in the medical adhesive tape or sheet of the present invention can use not only the film for a supporting substrate as a monolayer, but also a laminate that has been processed into a laminate film, if needed. The films to be laminated are not limited to the above film for a supporting substrate, and various plastic films other than this film, non-woven fabrics, porous films and the like can also be used. In the lamination, the films for a supporting substrate are simply laminated, and it is also preferable to laminate films or the like other than such films alternately. In this case, it is desirable that the films other than the film for a supporting substrate are exposed at one surface or both surfaces of the laminate.

Thus, by laminating films of different materials on the film for a supporting substrate, the functions of, for example, imparting (improving) an anchor effect, imparting a blocking resistance and preventing adhesive components from bleeding can be exhibited. The thickness of the film and the number of films laminated are adjusted so that those functions can be effectively exhibited. Further, the silicic acid compound can be contained in any layers of the laminate substance above.

It is preferable for the supporting substrate to adjust such that the stress relaxation ratio is 60% or less. When the stress relaxation ratio is adjusted to 60% or less, a tense feeling after adhering can be minimized. Further considering a person who is sensitive to irritation, it is desirable to set the stress relaxation ratio to 40% or less.

The medical adhesive tape or sheet according to the present invention is of such a construction that the adhesive layer is formed on either or both surface(s) of the supporting substrate thus obtained.

The adhesive used in the adhesive layer is not particularly limited and conventional adhesives used in general medical adhesive sheets can be used. One kind or two kinds or more of appropriate adhesives such as acrylic adhesives, rubber adhesives and silicone adhesives can be used.

In particular, considering the skin-irritating property, an acrylic adhesive is preferably used. Where the acrylic adhesive is used to the supporting substrate of the present invention, the stress relaxation property is further improved.

Those adhesives are applied to the supporting substrate by the conventionally known methods to form an adhesive layer. The thickness of the adhesive layer is not particularly limited, but the thickness is generally 10 to 200 μm, preferably 20 to 100 μm.

The first-aid adhesive tape of the present invention comprises a supporting substrate, which is provided with an absorbent pad at the central region on the surface of the adhesive layer formed on one surface of the supporting substrate. The absorbent pad used is selected from the known materials conventionally used. Examples of the absorbent pad used include gauze, woven fabrics, non-woven fabrics, a composite product of absorbent cotton and non-woven fabric and a composite product of absorbent cotton and knitted net.

Size of the absorbent pad varies depending on the size of the medical adhesive tape or the like, but it is preferable to adjust the size such that the adhesive layer of the adhesive sheet is exposed at least 2 to 3 mm at the periphery of the absorbent pad.

It is preferable in the first-aid adhesive tape of the present invention that the surface of the adhesive layer is covered with a separator in order to prevent the surface of the adhesive layer from contamination. The separator used is preferably a separator that is provided with a silicone release agent so that the separator can have good releasability from the adhesive layer containing an organosiloxane polymer.

According to the present invention, a supporting substrate that can relax to a low stress region for a relatively short stress relaxation time, as compared with the conventional supporting substrate that has been developed as a substitute of the vinyl chloride resin. Therefore, there can be provided a medical adhesive tape or sheet that has less physical irritation to a skin even if adhered for a long period of time as well as good adhesiveness to a skin and feeling.

As a result, there can be provided a wide variety of products such as medical rolled bandages, plasters, first-aid tapes, dressing materials, poultice and percutaneous absorption preparations that have as a supporting substrate a substitute for a vinyl chloride resin film.

Further, since the tape or sheet of the present invention contains the silicic acid compound, its heat resistance and moldability can be improved. As a result, heat treatment at high temperatures becomes possible, so that production rate is increased and the product can be provided at low costs. Further, since sterilization treatment under heating also becomes possible, a simple sterilization method is applicable, and the medical adhesive sheet or the first-aid adhesive tape that can be more easily used in medical workplaces can be provided.

Further, addition of resin modifiers or compatibilizers makes it easier to adjust blocking resistance and anchor property of the adhesive used, so that a medical adhesive sheet or tape and a first-aid adhesive tape that have good handling property and less adhesive residue can be provided.

EXAMPLES

Medical adhesive sheets according to the Examples were prepared using various supporting substrates, and the effect of the present invention was confirmed. However, it should be understood that the invention is not limited to the Examples. Unless otherwise indicated, all parts, percentages (%) are by weight. (76)

Preparation of Supporting Substrate

The following 15 kinds of materials were used as the thermoplastic resin: Homopolypropylene (homoPP) (trade name "Grand Polymer", E101P, a product of Grand Polymer Co.); Ethylene-methyl methacrylate copolymer resin (EMMA) (trade name "Acryft", WD20, a product of Sumitomo Chemical Co.); Polyisoprene type styrene elastomer (SIS) (trade name "Carififlex TR", TR1107, a product of Shell Chemical Co.); Low-density polyethylene (LDPE) (trade name "Petrethene", 339, a product of Tosoh Corporation); Ethylene-vinyl acetate copolymer (EVA) (trade name "Evatate", D2010F, a product of Sumitomo Chemical Co.); Ethylene propylene rubber (EPR) (trade name "JSREP", EP01P, a product of JSR Corporation); PP/EPR copolymer (trade name "Catalloy Adflex", KS-021P, KS-221P, KS-353P, products of Montell JPO Co.); Amorphous poly-α-olefin (trade name "Ubetac APAO", UT2780, a product of Ube Industry Co.); APAO/PP mixture (trade name "CAP", CAP350, a product of Ube Industry Co.); Styrene-based thermoplastic elastomer (trade name "Rabalon", SJ4460N, a product of Mitsubishi Corporation); and Polyester-based thermoplastic elastomer (trade name "Primalloy", A1600, a product of Mitsubishi Corporation); Acrylic rubber (trade name "Reocoat", H-624, Daiichi Lace Co.); and random polypropylene (randomPP) (trande name "Grand Polymer", S235, a product of Grand Polymer Co).

The following 6 kinds of materials were used as the silicic acid compound: Silica (trade name "Denka Fused Silica", FB-80, a product of Denki Kagaku Kogyo K.K.); Talc (trade name "Talc", MS-P, a product of Nippon Talc K.K.); Talc (trade name "Micro Ace", L-1, a product of Nippon Talc K.K.); A-type zeolite (trade name "Silton", DS, a product of Mizusawa Industrial Chemicals, Ltd.); A-type zeolite (trade name "Zeostar", NA-100P, a product of Nippon Chemical Industry Co.); and X-type zeolite (trade name "Mizukalizer", 13X Powder, a product of Mizusawa Industrial Chemicals, Ltd.).

The following materials were used as the compatibilizers/resin modifiers: Ethylene-acrylic acid ester-maleic anhydride copolymer (trade name "Bondine", AX-8390, a product of Atochem Co.); and crystalline polyolefin-polyethylene/butadiene-crystalline poleolefin (trade name "DYNARON", CEBC6200P, a product of JSR Corporation).

As the Comparative Examples, the same materials were used for the thermoplastic resin except that as the inorganic filler, the following two kinds of materials were used: Calcium carbonate (special grade chemical, a product of Wako Pure Chemical Industry); and Mica (trade name "Mica powder", A-21, a product of Yamaguchi Unmo Kogyousho).

Those thermoplastic resins, silicic acid compounds and compatibilizers/resin modifiers were blended at the blending ratio as shown in Tables 1 to 6 below to prepare films for a supporting substrate of Examples 1 to 30 and Comparative Examples 1 to 18.

The film for a supporting substrate was prepared in the following manner. A 20-liter pressure kneader was used. A can body temperature was heated to 125° C., and a base polymer (thermoplastic resin) was introduced therein. The can body was gradually heated and the base polymer was kneaded until the can body temperature reached 170° C. After elevating the temperature to 170° C., a silicic acid compound (or inorganic filler) was introduced therein, and the resulting mixture was kneaded for 30 minutes. Optionally, a compatibilizer or a resin modifier was introduced therein, and the resulting mixture was further kneaded for 30 minutes. Further, if desired, the mixture was formed into pellets.

Using the subject resin composition (resin pellets), films for a supporting substrate of Examples 16 and 17 as well as Comparative Example 11 shown in Table 3 were prepared by an extrusion molding method described below. The films for a supporting substrate other than the above were prepared by a rolling molding method described below.

Rolling Molding Method

Using a compression molding machine, the above resin composition (resin pellets) was pressed at a heating temperature of 150 to 220° C. under pressing pressure condition of 80 kgf/cm$^2$ for about 15 minutes. In this pressing operation, heating temperature and pressing pressure were adjusted such that the thickness of the film obtained was 80 to 100 μm.

Extrusion Molding Method T-Die Method

Twin-screw extrusion stretching machine (length of gap of T-die: 120 mm, width of clearance: 1 mm) was used. Cylinder temperature of the extruder was appropriately adjusted to be between 150° C. and 220° C. depending on the kind of the resin used. The resin composition (resin pellets) was extruded, and while cooling with cooling rolls, a film was formed by adjusting the rotational ratio of the subsequent two stretching rolls such that the thickness of the film was about 80 μm. Further, revolution rate of the stretching roll was adjusted in a range of 2 to 8 m/minute, and after stretching and film formation, the film was again passed through the cooling rolls and wound.

Preparation of Medical Adhesive Sheet

Each of the films for a supporting substrate obtained in Examples 14 and 21 as well as Comparative Example 8 was used as a supporting substrate in the form of a monolayer. An acrylic resin composed of acrylic acid and isooctyl acrylate (blending ratio 5:95 by weight) was applied to one surface of the film such that a thickness of an adhesive layer was 40 μm, thereby obtaining medical adhesive sheets of the Examples and the Comparative Example.

Preparation of First-Aid Adhesive Tape

Each of the medical adhesive sheets obtained above was cut into a size of 19 mm×72 mm, and a gauze pad having a size of 12 mm×20 mm was provided at the central area on the surface of the adhesive layer, thereby obtaining first-aid adhesive tapes of the Examples and the Comparative Example.

Evaluation Test of Supporting Substrate

Using various films for a supporting substrate obtained above, the following evaluation test was conducted. The film was cut into a size having a width of 20 mm and a length of 20 mm, and such a piece was used as a test sample. Using a tensile tester (Autograph AGS-100D, manufactured by Shimadzu Corporation), measurement was conducted under the conditions of room temperature of 23° C. and humidity of 65%. Prior to the measurement, the test sample was previously allowed to stand under the same conditions for 30 minutes or more. The results obtained are shown in Tables 1 to 6 below.

Initial Stress

A film was stretched at a tensile speed of 300 mm/minute using a tensile tester to measure changes in tensile stress value, and a stress-strain curve was obtained. Tensile stress (modulus, unit: gf/20 mm) at a tensile initial stage was then obtained from the stress-strain curve.

Elongation Percentage at Break

Tensile test was conducted under the same test conditions as above, elongation (%) at the time when a test sample brake was measured.

Elastic Modulus

Tensile test was conducted under the same test conditions as above, and a slope (gf/mm$^2$) of a straight line connecting two points of elongation of 0 mm and 2 mm in the above stress-strain curve.

Stress Relaxation Ratio

Using a tensile tester, a film was stretched at a tensile speed of 300 mm/min until a stretching ratio was 10%. Changes in tensile stress value with the passage of time were measured, and the stress relaxation ratios (%) were measured by the following equation.

Stress relaxation ratio (%)=(tensile stress after 5 minutes/initial tensile stress)×100

The initial tensile stress shows the maximum tensile stress value until 10% stretching from the initiation of pulling.

Stress Half Value Time

Using a tensile tester, a film was stretched at a tensile speed of 300 mm/min until a stretching ratio was 10%. Changes in tensile stress value with the passage of time were measured, and a stress relaxation curve was obtained. Time until the initial tensile stress was half was obtained from the stress relaxation curve. Pulling initiation time was expressed 0 hour.

Whitening Property

The presence or absence of whitening when the test sample was stretched in a state of elongation percentage of 10% for 5 minutes was visually judged.

Heat Resistance

The film for a supporting substrate was cut into a size having a width of 20 mm and a length of 50 mm. The resulting test sample was hung in a thermostat chamber at 120° C. for 60 minutes, and the presence or absence of deformation or shrinkage of the test sample was observed.

Evaluation Test of Medical Adhesive Sheet

Each of the medical adhesive sheets of the Examples and the Comparative Examples was cut into a size of 5 cm×5 cm (25 cm$^2$), and this was used as a sample for skin adhesion.

The samples for skin adhesion obtained were applied for 24 hours to the inside of upper arm (portion that is liable to have a rash) and the joint (bending portion) of 12 healthy persons, and adhesion feeling, skin adhesiveness and skin irritating property were evaluated according to 5 rank evaluation as shown in Table 7. Regarding the skin irritating property, evaluation was made for only the inside of upper arm, and the results obtained are shown in Table 7.

Evaluation Test of First-Aid Adhesive Tape

The first-aid adhesive tapes of the Examples and the Comparative Examples were wrapped around the second finger and the second joint of 12 healthy persons, and those persons lived a normal life. Adhesion feeling, skin adhesiveness and skin irritating property were evaluated according to 5 rank evaluation as shown in Table 8. The results obtained are shown in Table 8.

Test Results

As is apparent from Tables 1 to 6, the films for a supporting substrate according to the Examples can decrease the stress relaxation ratio without greatly increasing or decreasing the initial stress, and also can markedly decrease the stress half value time. Thus, it was confirmed to achieve the object of the present invention.

Further, as is apparent from Tables 7 and 8, the medical adhesive sheets and the first-aid adhesive tapes according to the Examples can obtain superior evaluation in either of adhesion feeling, skin adhesiveness and skin irritating property, as compared with the Comparative Examples.

TABLE 1

| | Base Polymer | Blending Ratio (Part) | Inorganic Filler | Blending Ratio (Part) | Modifier/ Compatibilizer |
|---|---|---|---|---|---|
| Comparative Example 1 | SIS | 100 | — | — | — |
| Example 1 | SIS | 60 | Zeolite DS | 40 | — |
| Comparative Example 2 | EMMA | 100 | — | — | — |
| Example 2 | EMMA | 60 | Zeolite DS | 40 | — |
| Comparative Example 3 | LDPE + EVA Blending Ratio 1:1 | 100 | — | — | — |
| Example 3 | LDPE + EVA Blending Ratio 1:1 | 60 | Zeolite NA-100P | 40 | — |
| Comparative Example 4 | homoPP | 80 | — | — | Bondine AX8390 |
| Example 4 | homoPP | 40 | Zeolite NA-100P | 40 | Bondine AX8390 |
| Comparative Example 5 | HomoPP + EPR Blending Ratio 1:1 | 100 | — | — | — |
| Example 5 | HomoPP + EPR Blending Ratio 1:1 | 50 | Zeolite NA-100P | 50 | — |
| Example 6 | Catalloy KS-221P | 50 | Zeolite NA-100P | 50 | — |

TABLE 1-continued

|  | Blending Ratio (Part) | Elongation Percentage at Break (%) | Initial Stress (gf/20 mm) | Stress Relaxation Ratio (%) | Stress Half Value Time (Sec) |
|---|---|---|---|---|---|
| Comparative Example 1 | — | 768 | 31 | 74 | 500< |
| Example 1 | — | 610 | 62 | 51 | 454< |
| Comparative Example 2 | — | 511 | 764 | 65 | 500< |
| Example 2 | — | 120 | 1185 | 39 | 82 |
| Comparative Example 3 | — | 692 | 1520 | 67 | 500< |
| Example 3 | — | 2 | 2800 | 32 | 18 |
| Comparative Example 4 | 20 | 58 | 3725 | 53 | 425 |
| Example 4 | 20 | 90 | 3214 | 39 | 52 |
| Comparative Example 5 | — | 210 | 1162 | 49 | 135 |
| Example 5 | — | 42 | 1080 | 38 | 44 |
| Example 6 | — | 45 | 986 | 25 | 3 |

TABLE 2

|  | Base Polymer | Blending Ratio (Part) | Inorganic Filler | Blending Ratio (Part) | Modifier/ Compatibilizer | Blending Ratio (%) |
|---|---|---|---|---|---|---|
| Comparative Example 6 | Catalloy KS-021P | 100 | — | — | — | — |
| Comparative Example 7 | Catalloy KS-021P | 80 | Titanium Oxide | 20 | — | — |
| Example 7 | Catalloy KS-021P | 80 | Zeolite NA-100P | 20 | — | — |
| Comparative Example 8 | Catalloy KS-353P | 100 | — | — | — | — |
| Comparative Example 9 | Catalloy KS-353P | 60 | Calcium carbonate | 40 | — | — |
| Example 8 | Catalloy KS-353P | 60 | Zeolite NA-100P | 40 | — | — |
| Comparative Example 10 | Catalloy KS-221P | 100 | — | — | — | — |
| Example 9 | Catalloy KS-221P | 60 | Silica | 40 | — | — |
| Example 10 | Catalloy KS-221P | 60 | Talc Microace | 40 | — | — |
| Example 11 | Catalloy KS-221P/ Reocoat H-624 | 60 | Talc Microace | 40 | — | — |
| Example 12 | Catalloy KS-221P | 60 | Zeolite 13X | 40 | — | — |
| Example 13 | Catalloy KS-221P | 80 | Zeolite NA-100P | 20 | — | — |
| Example 14 | Catalloy KS-221P | 60 | Zeolite NA-100P | 40 | — | — |
| Example 15 | Catalloy KS-221P | 40 | Zeolite NA-100P | 40 | Bondine AX8390 | 20 |

|  | Initial Stress (gf/20 mm) | Stress Relaxation Ratio (%) | Stress Half Value Time (Sec) |
|---|---|---|---|
| Comparative Example 6 | 1171 | 46 | 33 |
| Comparative Example 7 | 1250 | 44 | 36 |
| Example 7 | 1089 | 32 | 15 |
| Comparative Example 8 | 542 | 47 | 139 |
| Comparative Example 9 | 562 | 47 | 141 |
| Example 8 | 550 | 36 | 16 |

TABLE 2-continued

|  | | | |
|---|---|---|---|
| Comparative Example 10 | 825 | 45 | 45 |
| Example 9 | 1017 | 26 | 4 |
| Example 10 | 1636 | 28 | 5 |
| Example 11 | 1234 | 28 | 6 |
| Example 12 | 868 | 27 | 3 |
| Example 13 | 920 | 31 | 12 |
| Example 14 | 880 | 24 | 4 |
| Example 15 | 742 | 35 | 28 |

TABLE 3

| | Base Polymer | Blending Ratio (Part) | Inorganic Filler | Blending Ratio (Part) | Modifier/ Compatibilizer | Blending Ratio (Part) |
|---|---|---|---|---|---|---|
| Comparative Example 11 | Catalloy KS-221P | 100 | — | — | — | — |
| Example 16 | Catalloy KS-221P | 60 | Zeolite NA-100P | 40 | — | — |
| Example 17 | Catalloy KS-221P | 40 | Zeolite NA-100P | 40 | Bondine AX8390 | 20 |

| | Elongation Percentage At Break (%) | Elastic Modulus (gf/mm$^2$) | Stress Relaxation Ratio (%) | Stress Half Value Time (Sec) | Whitening Property |
|---|---|---|---|---|---|
| Comparative Example 11 | 650 | 3582 | 39 | 40 | Transparent |
| Example 16 | 402 | 3240 | 33 | 12 | Slightly Whitening |
| Example 17 | 450 | 1987 | 36 | 28 | Transparent |

TABLE 4

| | Base Polymer | Blending Ratio (Part) | Inorganic Filler | Blending Ratio (Part) | Modifier/ Compatibilizer | Blending Ratio (Part) |
|---|---|---|---|---|---|---|
| Comparative Example 12 | Catalloy KS-221P | 100 | — | — | — | — |
| Example 18 | Catalloy KS-221P | 60 | Talc Microace | 40 | — | — |
| Example 19 | Catalloy KS-221P | 40 | Talc Microace | 60 | — | — |
| Example 20 | Catalloy KS-221P | 45 | Talc Microace | 45 | DYNARON 6200P | 10 |
| Comparative Example 13 | APAO UT2780 | 100 | — | — | — | — |
| Example 21 | APAO UT2780 | 60 | Talc Microace | 40 | — | — |
| Example 22 | APAO UT2780 | 40 | Talc Microace | 60 | — | — |
| Example 23 | APAO UT2780 | 60 | Calcined Talc POLESTAR 450 | 40 | — | — |

| | Elongation Percentage at Break (%) | Initial Stress (gf/20 mm) | Stress Relaxation Ratio (%) | Stress Half Value Time (Sec) | Whitening Property |
|---|---|---|---|---|---|
| Comparative Example 12 | 580 | 1170 | 39 | 32 | Transparent |
| Example 18 | 25 | 2005 | 27 | 5 | Whitened |
| Example 19 | 12 | 2380 | 23 | 3 | Whitened |
| Example 20 | 45 | 1509 | 31 | 16 | Transparent |
| Comparative Example 13 | 720 | 64 | 31 | 12 | Transparent |
| Example 21 | 250 | 78 | 23 | 3 | Transparent |
| Example 22 | 180 | 110 | 18 | 1 | Transparent |
| Example 23 | 200 | 80 | 27 | 7 | Transparent |

TABLE 5

|  | Base Polymer | Blending Ratio (Part) | Inorganic Filler | Blending Ratio (Part) | Modifier/ Compatibilizer | Blending Ratio (Part) |
|---|---|---|---|---|---|---|
| Comparative Example 14 | APAO + homoPP Blending Ratio 1:1 | 100 | — | — | — | — |
| Example 24 | APAO + homo PP Blending Ratio 1:1 | 60 | Zeolite NA-100P | 40 | — | — |
| Example 25 | APAO + random PP Blending Ratio 1:1 | 60 | Zeolite NA-100P | 40 | — | — |
| Example 26 | APAO + homoPP Blending Ratio 1:1 | 40 | Zeolite NA-100P | 60 | — | — |
| Comparative Example 15 | APAO + homoPP Blending Ratio 2:1 | 30 | Zeolite NA-100P | 70 | — | — |
| Comparative Example 16 | CAP350 | 100 | — | — | — | — |
| Example 27 | CAP350 | 50 | Talc Microace | 50 | — | — |
| Example 28 | CAP350 | 50 | Zeolite NA-100P | 50 | — | — |

|  | Initial Stress (gf/20 mm) | Stress Relaxation Ratio (%) | Stress Half Value Time (Sec) | Heat Resistance 120° C., 60 min |
|---|---|---|---|---|
| Comparative Example 14 | 1350 | 45 | 65 | Slightly shrinked |
| Example 24 | 1285 | 22 | 18 | No Change |
| Example 25 | 1100 | 21 | 13 | No Change |
| Example 26 | 1311 | 15 | 6 | No Change |
| Comparative Example 15 | * | * | * | * |
| Comparative Example 16 | 751 | 43 | 80 | Slightly shrinked |
| Example 27 | 1210 | 16 | 41 | No Change |
| Example 28 | 951 | 14 | 35 | No Change |

*Breakage occurred before the film was elongated so that measurement was impossible (the film was poor in stretchability and flexibility and thus the feeling was poor).

TABLE 6

|  | Base Polymer | Blending Ratio (Part) | Inorganic Filler | Blending Ratio (Part) | Modifier/ Compatibilizer | Blending Ratio (Part) |
|---|---|---|---|---|---|---|
| Comparative Example 17 | Rabalon SJ4460N | 100 | — | — | — | — |
| Example 29 | Rabalon SJ4460N | 50 | Talc MS-P | 50 | — | — |
| Comparative Example 18 | Primalloy A1600 | 100 | — | — | — | — |
| Example 30 | Primalloy A1600 | 50 | Talc MS-P | 50 | — | — |

|  | Elongation Percentage at Break (%) | Elastic Modulus (gf/20 mm) | Stress Relaxation Ratio (%) | Stress Half Value Time (Sec) |
|---|---|---|---|---|
| Comparative Example 17 | 710 | 1350 | 70 | 500< |
| Example 29 | 560 | 2560 | 38 | 18 |
| Comparative Example 18 | 780 | 1280 | 82 | 500< |
| Example 30 | 480 | 2800 | 37 | 20 |

TABLE 7

| Supporting Substrate | Adhesion Feeling | | Skin Adhesiveness | | Skin Irritating Property | |
|---|---|---|---|---|---|---|
| | Upper Arm | Joint | Upper Arm | Joint | Upper Arm | Joint |
| Example 14 | 4.6 | 4.8 | 4.7 | 4.5 | 4.8 | — |
| Example 21 | 4.9 | 4.5 | 4.9 | 4.8 | 4.6 | — |
| Comparative Example 8 | 3.8 | 4.0 | 3.5 | 4.2 | 3.2 | — |

Adhesion Feeling: 5(Good)-4-3(Average)-2-1(Poor)
Skin Adhesiveness: 5(Good)-4-3(Average)-2-1(Poor)
Skin Irritating Property: 5(Good)-4-3(Average)-2-1(Poor)

TABLE 8

| Supporting Substrate | Adhesion Feeling | Skin Adhesiveness | Skin Irritating Property |
|---|---|---|---|
| Example 14 | 4.5 | 4.6 | 4.8 |
| Example 21 | 4.9 | 4.8 | 4.5 |
| Comparative Example 8 | 3.2 | 3.0 | 4.0 |

Adhesion Feeling: 5(Good)-4-3(Average)-2-1(Poor)
Skin Adhesiveness: 5(Good)-4-3(Average)-2-1(Poor)
Skin Irritating Property: 5(Good)-4-3(Average)-2-1(Poor)

The invention may be embodied in other specific forms without departing from the spirit or essential characteristics thereof. Therefore, the present embodiment is to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A medical adhesive tape for adhering onto a skin surface comprising a supporting substrate and an adhesive layer directly or indirectly laminated thereon, wherein said supporting substrate comprises a composition which comprises 100 parts by weight of a thermoplastic resin and 10 to 200 parts by weight of a silicic acid compound, wherein said medical adhesive tape is adhereable to a skin surface, and wherein said supporting substrate has a stress relaxation ratio of 60% or less.

2. The medical adhesive tape as claimed in claim 1, wherein said silicic acid compound is at least one selected from the group consisting of zeolite, talc and silica.

3. The medical adhesive tape as claimed in claim 1, wherein said thermoplastic resin is at least one member selected from the group consisting of a polypropylene resin, a blend of a polypropylene resin and an elastomer, and a copolymer of a polypropylene resin and an elastomer.

4. The medical adhesive tape as claimed in claim 3, wherein the polypropylene resin, or the copolymer of a polypropylene resin and an elastomer is amorphous or low crystalline.

5. The medical adhesive tape as claimed in claim 4, wherein the amorphous or low crystalline polyolefin resin is present in an amount of 30 to 100% by weight based on the total weight of film-forming materials for a supporting substrate.

6. The medical adhesive tape as claimed in claim 1, wherein said supporting substrate further comprises a resin modifier.

7. The medical adhesive tape as claimed in claim 6, wherein the resin modifier is present in an amount of 0.1 to 40% by weight based on the total weight of the film-forming resin composition.

8. The medical adhesive tape as claimed in claim 6, wherein said resin modifier is at least ore selected from the group consisting of a hydrogenated product of styrene-butadiene copolymer or its maleic acid-modified product, polystyrene-polyethylene butylene-crystalline polyolefin, crystalline polyolefin-polyethylene butylene-crystalline polyolefin, ethylene-ethyl acrylate copolymer, ethylene-acrylic acid ester-maleic anhydride copolymer, ethylene-methacrylic acid glycidyl ester copolymer, maleic anhydride graft polypropylene, maleic anhydride graft ethylene-polypropylene copolymer, acrylic acid graft polypropylene, ethylene-vinyl acetate copolymer, ethylene-vinyl acetate/ethylene-propylene-diene/polyolefin graft copolymer, metal salts of ethylene-methacrylic acid copolymer and chlorinated paraffin.

9. A first-aid adhesive tape comprising the medical adhesive tape as claimed in claim 1, and an absorbent pad provided at a central region on a surface of the adhesive layer thereof.

* * * * *